United States Patent [19]

Rifu

[11] Patent Number: 4,477,728
[45] Date of Patent: Oct. 16, 1984

[54] RADIATION DETECTOR

[75] Inventor: Toshihiro Rifu, Ootawara, Japan

[73] Assignee: Tokyo Shibaura Denki Kabushiki Kaisha, Kawasaki, Japan

[21] Appl. No.: 302,455

[22] Filed: Sep. 15, 1981

[30] Foreign Application Priority Data

Sep. 18, 1980 [JP] Japan .................. 55-129464

[51] Int. Cl.$^3$ ............................................. G01T 1/185
[52] U.S. Cl. .................. 250/385; 250/252.1; 378/157
[58] Field of Search .............. 250/252.1, 394, 385, 250/368; 378/57, 79, 156, 207, 159, 56, 157, 158

[56] References Cited

U.S. PATENT DOCUMENTS

| | | | |
|---|---|---|---|
| 2,831,980 | 4/1958 | Howell | 250/252.1 |
| 2,842,672 | 7/1958 | Thomsen | 250/394 |
| 3,665,191 | 5/1972 | Moody | 250/368 |
| 3,755,672 | 8/1973 | Edholm et al. | 378/158 |
| 4,041,315 | 8/1977 | Hounsfield . | |
| 4,051,379 | 9/1977 | Zacher | 250/385 |
| 4,075,527 | 2/1978 | Cummings | 250/385 |
| 4,288,695 | 9/1981 | Walters et al. | 378/159 |

FOREIGN PATENT DOCUMENTS 871284 5/1971 Canada ..................... 350/314

Primary Examiner—Alfred E. Smith
Assistant Examiner—Carolyn E. Fields
Attorney, Agent, or Firm—Finnegan, Henderson, Farabow, Garrett & Dunner

[57] ABSTRACT

A radiation detector adapted to be used with a computerized tomographic apparatus, wherein filters prepared from a radiation-absorbing material are provided on the outside of a radiation-permeable window in the positions facing radiation-detecting cells. The filters compensate for differences between the radiation-detecting properties of the detection cells, thereby equalizing said radiation-detecting properties.

11 Claims, 8 Drawing Figures

RADIATION DETECTOR

BACKGROUND OF THE INVENTION

This invention relates to a radiation detector most adapted to be used with a computerized tomography.

A computerized tomographic apparatus for displaying the sectional plane of a human body by applying radiation such as X-rays is known as the apparatus for examining the human body.

This computerized tomographic apparatus fundamentally comprises, as shown in FIG. 1, and X-ray source 4 for emitting a fan-shaped X-ray beam in the form of a fan to surround a foreground subject 2 and a detector 6 fomred of a large number of X-ray detecting cells. The X-ray source 4 and X-ray detector 6 are rotated around the foreground subject 2 in the same direction at the same circumferential speed, thereby irradiating X-rays in various directions. X-ray photographed data on the foreground subject 2 which have been detected by the detector 6 are converted into electric signals. The converted electric signals are analyzed by an electronic computer, thereby figuring out X-ray absorption rates. An image of sectional plane of a foreground subject is constructed again in accordance with tone levels corresponding to said X-ray absorption rates.

The detector holds a large number of radiation-detecting cells defined between a pair of electrode plates. Each radiation-detecting cell constitutes an ionization chamber. X-ray energy entering the radiation-detecting cell through an X-ray permeable window is detected in the form of ionization current. Ionization current running through each X-ray path are integrated for a prescribed length of time. The integrated ionization currents are discharged in a discharge circuit having a prescribed time constant. The time of said discharge is taken as X-ray photographed data for each X-ray path. When collection of data at a position denoting a given circumferential angle is brought to an end, then collection of data is commenced at a position of the succeeding circumferential angle.

To elevate the radiation-detecting property of such a computerized tomographic apparatus as described above, it is necessary to enable the detector to absorb introduced radiation at a high rate. To this end, therefore, the detector is filled with a very stable heavy element having a large X-ray absorption coefficient, for example xenon or krypton with high pressure. Further to assure the stable detection of the detector, it is necessary that where the detector receives a fixed dosage of radiation, the respective cells constituting said detector be so arranged as to always send forth the same output. However, it has been impossible to fix the property of several hundreds of cells constituting the detector. Particularly, irregularities in the width of the interval between the electrode plates and the inclination of said electrode plates seriously affect the property of the detector cells. To date, therefore it has been impossible to realize a stable detection property by any other means than by manufacturing a detector with as great care as possible to equalize the property of the respective cells. Even if a single cell included in several hundred cells has a different X-ray detection property from that of the other cells, then a reconstructed image is contaminated by an artifact. At present, therefore, it is most earnestly demanded to develop a detector having an extremely stable property.

SUMMARY OF THE INVENTION

It is accordingly the object of this invention to provide a radiation detector which prevents the constituent cells from indicating different radiation-detecting properties, thereby assuring a stable radiation-detecting property as a whole.

To attain the above-mentioned object, this invention provides a radiation detector which comprises radiation absorbing filters mounted on the radiation permeable window of the radiation detector body in such positions as face the respective detection cells, thereby effecting compensation for differences between the radiation-detecting properties of the respective constituent cells.

DETAILED DESCRIPTION OF THE PREFERRED EMBODIMENTS

Figure 1:
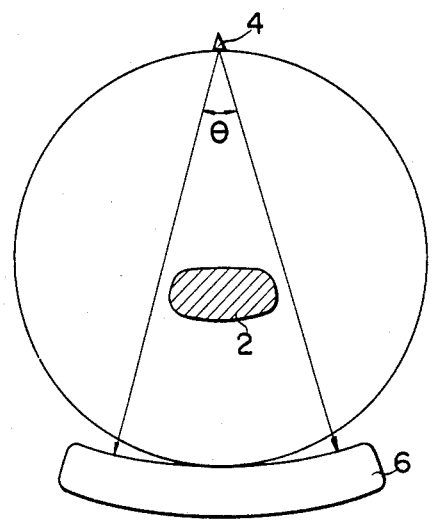
FIG. 1 is a schematic plan view of a computerized tomographic apparatus.
Figure 2:
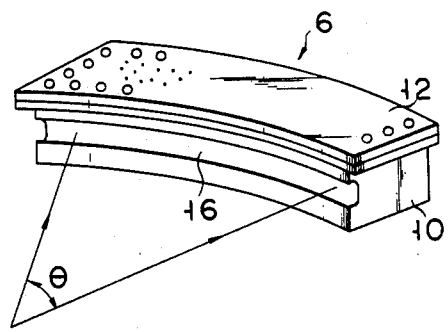
FIG. 2 is an oblique view of a radiation detector embodying this invention.
Figure 3:
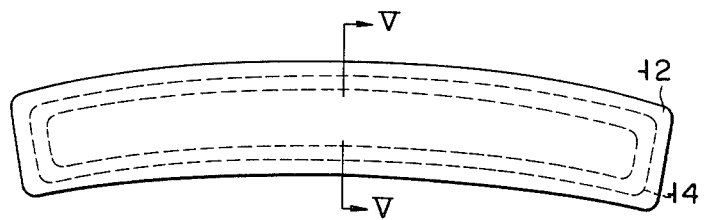
FIG. 3 is a front view of said radiation detector.
Figure 4:
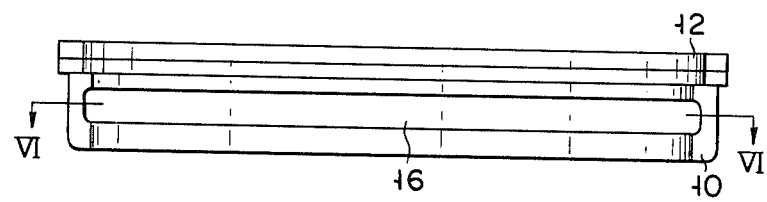
FIG. 4 is a plan view of said radiation detector.

As shown in FIGS. 2 and 4, a radiation detector embodying this invention comprises a body 10 provided with a cavity 14 for holding a large number of detection cells and a cap 12 for sealing the opening of the body 10. The cavity 14 of the radiation detector 6 not only holds a large number of detection cells (not shown), but also is filled with an ionizable gas, for example, xenon. An X-ray permeable window 16 whose thickness is sufficiently reduced to enable X-ray energy to reach the detection cells is formed on part of the X-ray receiving side of the X-ray detector 6 with a sufficient width to match the angle $\Lambda$ at which the fan-shaped X-ray beams are expanded.

Figure 5:
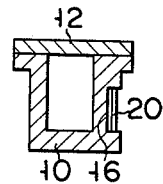
FIG. 5 is a section view on line V—V of said radiation detector.
Figure 6:
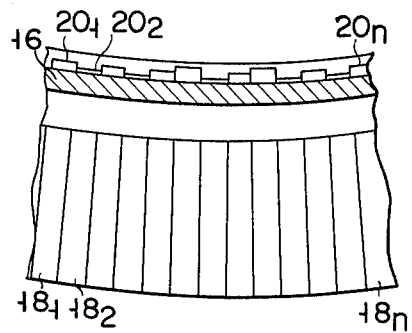
FIG. 6 is a sectional view on line VI—VI of FIG. 4.

The body 10 contains a long row of numerous consecutively arranged detection cells $18_1, \ldots, 18_n$ each defined by a pair of electrode plates with a certain space allowed from the X-ray permeable window 16 as shown in FIGS. 5 and 6. Filters $20_1, \ldots, 20_n$ are mounted on the outside of the window 16 in positions facing the detection of $18_1, \ldots, 18_n$ of the respective channels. The filter is prepared from X-ray absorbing material such as metals, for example, aluminum, copper and iron or synthetic resins, for example, Teflon and acrylic resin. The filters $20_1, \ldots, 20_n$ are formed with a sufficient thickness to eliminate differences in the X-ray detecting property of the corresponding cells $18_1, \ldots, 18_n$.

The process of fitting the filters $20_1, \ldots, 20_n$ to the outside of the window 16 is not subject to any particular limitation. But the application of an adhesive is simple and preferred to effect said fitting. Each detection cell is chosen to have a width of about 1 mm. If the filters $20_1, \ldots, 20_n$ are so set as to enable 70% of the width thereof to cover the corresponding detection cells $18_1, \ldots, 18_n$, the sufficient compensation can be assured for changes in the X-ray detecting properties of the respective cells $18_1, \ldots, 18_n$. When, therefore, mounted on the outside of the window 16, the filter $20_1, \ldots, 20_n$ can be displaced up to about 0.5 mm from the position corresponding to the detection cells $18_1, \ldots, 18_n$. Since the filters $20_1, \ldots, 20_n$ are fitted to the outside of the window 16 after the assembly of the radiation detector 6, not only said fitting but also compensation for changes in the X-ray detecting properties of the cells $18_1, \ldots, 18_n$ can be effected with great ease.

Description is now given of the process of making compensation for differences between the X-ray detecting properties of the respective cells $18_1, \ldots, 18_n$ of the radiation detector 6 which result from the quality and dosage of X-rays applied.

Figure 7:
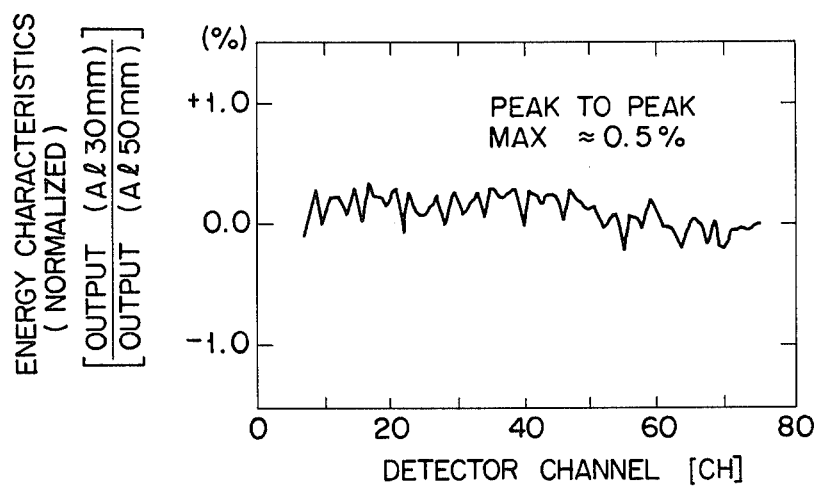
FIG. 7 graphically indicates the normalized energy of said detector.
Figure 8:
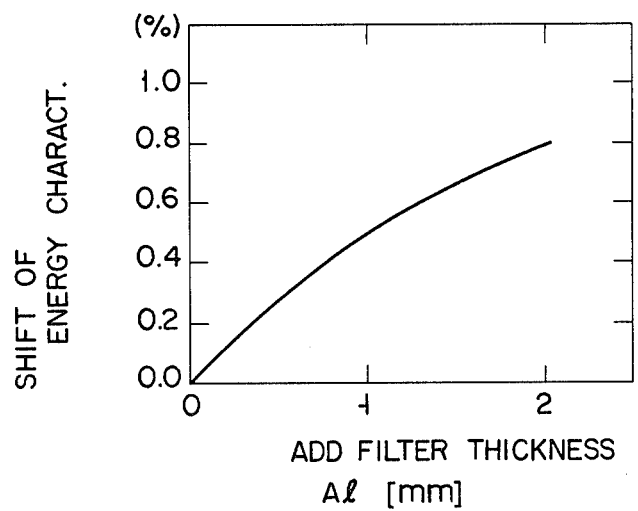
FIG. 8 graphically shows relationship between the thickness of an aluminium filter and changes in the energy characteristic of the detector.

A radiation detector was manufactured by the conventional process. Measurements were made of the properties of the respective cells of detecting the average X-ray energy with aluminum phantoms 30 mm and 50 mm thick used as a foreground subject. The X-ray detecting property of each detection cell measured by using the aluminium phantom 30 mm thick was divided by that of the same cell measured by using the phantom 50 mm thick to obtain the normalized energy characteristics of the respective cells, the results being set forth in FIG. 7. As seen from FIG. 7, the maximum peak-to-peak difference between the X-ray detecting properties of the respective cells was about 0.5%. Where the difference rose above 0.1%, then an artifact was likely to arise. In such case, it has hitherto been necessary to dismember the radiation detector for adjustment. An aluminium filter was provided for the respective cells to reduce each difference of normalized radiation-detecting properties to that of the detection cell which indicated the lowest peak in the radiation detecting property. Determination was made of the relationship between the thickness of an aluminium filter and the changes which appeared in the X-ray detecting properties of the respective cells after the application of the filter, the results being set forth in FIG. 8. The required thickness of an aluminium filter to compensate for differences between the X-ray detecting properties of the respective cells was determined from FIG. 8. It was shown that a detector cell which indicated a difference of 0.5% in the radiation detecting property from the standard lowest level had to be provided with an aluminium filter having a thickness of 1 mm.

The foregoing description refers to the case where a filter was provided separately from a radiation permeable window. However, the window itself may be changed in thickness. For instance, it is possible to reduce the thickness of the window facing the other cells than the detection cell having the maximum peak of FIG. 7 in order to assure coincidence between the property of said cell and those of the other cells. Since the window is prepared from an X-ray-absorbing material, a radiation permeable window thus machined has the same function as that which is provided with a filter.

This invention can compensate easily and with high precision for difference between the radiation detecting properties of hundreds of detection cells constituting a radiation detector, which result from changes in the quality and dosage of X-rays applied. Once the detector has been manufactured, compensation for differences between the radiation-detecting properties of the respective detection cells has hitherto been impossible, except when the detector is dismembered for adjustment. However, this invention makes it possible to easily compensate for the differences of the radiation-detecting properties of the respective detection cells, without dismembering the detector.

What is claimed is:

1. A radiation detector for sensing radiation transmitted through a subject to be examined comprising:
    a body;
    a plurality of radiation detection cells arranged side-by-side along the length of the body for converting radiation recieved by the respective cells into electrical signals representative of the radiation absorption properties of the subject, not all of the plurality of radiation detection cells having identical radiation detection characteristics;
    a radiation permeable window formed over the plurality of radiation detection cells, and
    a plurality of filters of radiation absorbing material mounted on the radiation permeable window, said filters being aligned with respective radiation detection cells for adjusting the intensity of radiation incident on each respective cell, each respective filter having a radiation absorbing property that standardizes the radiation detection characteristics of the respective cell with which it is aligned so that when the detector receives a standard dosage of radiation, each cell will produce the same electrical signal.

2. The radiation detector according to claim 1, wherein the plurality of filters are made of a metal.

3. The radiation detector according to claim 2, wherein the plurality of filters are prepared from material selected from the group consisting of aluminium, copper and iron.

4. The radiation detector according to claim 2, where the plurality of filters are prepared from material selected from the group consisting of Teflon and acrylic resin.

5. The radiation detector according to claim 1, wherein the plurality of filters are attached to the exterior surface of the radiation permeable window by an adhesive.

6. The radiation detection cells of claim 1 wherein each cell includes a pair of electrodes and a material having a large radiation absorption coefficient between the electrodes.

7. The radiation detector of claim 6 wherein said material is xenon.

8. The radiation detector of claim 6 wherein said material is krypton.

9. The radiation detection cells of claim 1 wherein the plurality of filters are designed to make the normalized radiation detection characteristics of each cell equal to the normalized radiation detection characteristics of the cell having the lowest normalized radiation detection characteristics when no filters are aligned with the radiation detection cells.

10. A radiation detector comprising:
    a body having a cavity;
    a radiation permeable window;
    a plurality of spaced conductive electrode members being arranged adjacent to each other in a predetermined order in the cavity, some of the members cooperating with adjacent members to define ionization cells filled with ionizable gas, the cells being arranged such that radiation which passes through the window enters the cells; and a plurality of filters of radiation absorbing material mounted on the radiation permeable window, said filters being aligned with respective radiation detection cells and each filter being sufficiently thick so that the radiation absorbing properties of each filter standardizes the radiation detection characteristics of the respective cell with which it is aligned so that when the detector receives a standard dosage of radiation, each cell will produce the same electrical signal.

11. A radiation detector for sensing x-ray radiation transmitted through a subject to be examined comprising:

a body;

a plurality of x-ray radiation detection cells arranged side-by-side along the length of the body for converting x-ray radiation received by the respective cells into electrical signals representative of the radiation absorption properties of the subject, not all of the plurality of radiation detection cells having identical x-ray radiation detection characteristics;

a x-ray radiation permeable window formed over the plurality of radiation detection cells; and a plurality of filters of x-ray radiation absorbing material mounted on the exterior surface of the radiation permeable window, said filters being aligned with respective radiation detection cells and each filter being sufficiently thick so that the radiation absorbing properties of each filter standardizes the radiation detection characteristics of the respective cell with which it is aligned so that when the detector receives a standard dosage of x-ray radiation, each cell will produce the same electrical signal.

* * * * *